United States Patent [19]

Kupchan et al.

[11] 3,969,369

[45] July 13, 1976

[54] BRUCEANTIN

[75] Inventors: S. Morris Kupchan, Charlottesville, Va.; Ronald W. Britton, Camlachie, Canada

[73] Assignee: Research Corporation, New York, N.Y.

[22] Filed: June 20, 1973

[21] Appl. No.: 371,634

[52] U.S. Cl. .......................... 260/343.2 R; 424/279; 424/195
[51] Int. Cl.² ........................................ C07D 311/20
[58] Field of Search ............................. 260/343.2 R

[56] References Cited
OTHER PUBLICATIONS

Cancer Chemotherapy Reports, Part 3, vol. 3, No. 2, p. 9 (Protocol 1.200), Sept. 1972.

Drug Research and Development Instruction 14, Cancer Treatment, National Cancer Institute, Bethesda, MD.

*Primary Examiner*—John M. Ford
*Attorney, Agent, or Firm*—Behr & Woodbridge

[57] ABSTRACT

There is provided a novel simaroubolide derived from *Brucea antidysenterica* which possesses high and surprising anti-leukemic activity at dosage levels of micrograms per kilogram body weight.

**5 Claims, No

BRUCEANTIN

The invention described herein was made in the course of work under grant or award from the Department of Health, Education and Welfare.

DESCRIPTION OF THE PRIOR ART

The botanical literature reports that *Brucea antidysenterica* Lam leaves and roots have been powdered for salve for use against cancerous tumors in its areas of origin, Eritrea and Ethiopia (Cortesi, Rass. Econ. delle Colonie (Rome) 24, 71-126 (1936)). It is further reported that the powder of the wood has been sold in Ethiopia for the ostensible purpose of curing tumors and cancer (Baldrati, Piate Officinali dell'Africa Orientale, 131 (1946)). These references are cited in Lloydia, 34, 204 (1971), at page 221-2.

Compounds of related structure namely bruceine B and bruceolide have been reported (Polansky, et al, Experientia, 23, 424 (1967). Anti-tumor activity of another simaroubolide has been reported (Wall and Wani, Int. Symp. Chem. Nat. Prod., 7th Abstracts, E138, 614 (1970)).

Heretofore however no active factor of unquestioned anti-leukemic activity has been isolated from *Brucea antidysenterica* Mill.

SUMMARY OF THE INVENTION

Ethanolic extracts of *Brucea antidysenterica* are subjected to a series of extraction, chromatographic and purification steps to yield inter alia bruceantin (1), bruceantarin (2) and iso-Bruceine B (6). The general formula of the compounds discussed herein is shown below.

1, R=OC, $R_2$=H, $R_3$=OH, (with CH(CH$_3$)$_2$ substituent)
2, R=OCC$_6$H$_5$, $R_2$=H, $R_3$=OH
3, R=OCCH$_3$, $R_2$=H, $R_3$=OH
4, R=H, $R_2$=H, $R_3$=OH
5, R=OCCH$_2$CHCH
   CH(CH$_3$)$_2$, $R_2$=H, $R_3$=OH
6, R=OOCH$_3$, $R_2$=OH, $R_3$=H In the process of isolation the stem bark of *Brucea antidysenterica* Mill is extracted with 95% ethanol and subjected to a series of extractions, partitions, and column fractionations shown and outlined in FIGS. I – III and discussed in greater detail hereinbelow. The extract was tested for anti-tumor activity in vitro against cells derived from human carcinoma of the nasopharynx (KB) and against two standard animal tumor systems well recognized in the testing arts. Bruceantin demonstrates significant anti-leukemic activity in the microgram/kilogram level, the level at which toxicity against the mammalian system itself is not a significant consideration.

FIG. 1 showing the extraction step is as follows:

```
                          Stage I
               Brucea Antidysenterica
                        │ Ethanol
                        ▼
            ┌──────────────────────────────┐
            │   "A" - Ethanol    Extract   │
            └──────────────────────────────┘
                   Chloroform/Water
            ┌──────────┴──────────────┐
   ┌────────────────────┐      ┌──────────────────┐
   │ "B" Chloroform Extract │  │ "C" Water Extract │
   └────────────────────┘      └──────────────────┘
            │
       10% Aqueous
     Methanol/Pat. Ether
   ┌────────┴──────────────┐
┌──────────────┐      ┌─────────────────────┐
│ "D" Petroleum│      │    10% Aqueous      │
│ Ether Extract│      │  Methanol Extract   │
└──────────────┘      └─────────────────────┘
                              │
                       Water/Carbon
                       Tetrachloride
            ┌─────────────────┴─────────┐
   ┌────────────────────┐      ┌──────────────┐
   │ 20% aqueous        │      │ "E" Carbon   │
   │ Methanol Extract   │      │ Tetrachlor-  │
   └────────────────────┘      │ ide Extract  │
            │                  └──────────────┘
      Water/Chloroform
   ┌────────┴──────────────┐
┌──────────────┐      ┌────────────────────┐
│ "F" Chloroform│     │ "G" 40% Aqueous    │
│ Extract       │     │ Methanol           │
└──────────────┘      └────────────────────┘
        │
     Stage II
```

Stage II

```
F  (chromatography on SilicAR CC-7)
│  CHCl₃
├─→ discard
│  0.5% methanol/chloroform (∼ 5 c.v.)
├─→ discard
│  1 % methanol/chloroform (∼ 5 c.v.)
├─→ discard
│  1% methanol/chloroform (∼5 c.v.)
├─→ bruceantin + dehydrobruceantin
│  1% methanol/chloroform (∼ 1–2 c.v.)
├─→ bruceantin + bruceantarin
│  1% methanol/chloroform (∼ 1–2 c.v.)
└─→ J
```

Stage III (a)

```
H  (chromatography by SilicAR CC-7)
│  3 → 20% ether benzene → discard

│  30% ether benzene (∼4–5 c.v.) trace (e)

│  30% ether benzene (∼8–10 c.v.) Bruceantin (f) (1)

│  30% ether benzene (∼4–5 c.v.) + dehydrobruceantin
                                         (g) (5)
```

Stage III (b)

```
I  (chromatography by SilicAR CC-7)
│  30% ether/benzene (∼20 c.v.) bruceantarin (2)

│  30% ether/benzene (∼16 c.v.) novel simaroubolide

│  30% ether/benzene (∼20 c.v.) isobruceine B (6)
```

DESCRIPTION OF THE PREFERRED EMBODIMENTS

In the process of the present invention dried ground stem bark of *Brucea antidysenterica* Will. is extracted with several batches of the lower alkanol, suitably ethanol, most preferably 95% ethanol. The extracts combined and the solvent removed, suitably by evaporation to yield a residue (A) which is then partitioned between chloroform and water. The chloroform extract (B) is retained, and the solvent removed, suitably by evaporation.

The residue (B) is then partitioned between 10% aqueous methanol/petroleum ether (that is to say, a water/methanol mixture containing 10% by volume of water and 90% by volume of methanol). The petroleum ether portion is discarded and sufficient water added to raise the dilution of the methanol to 20% aqueous methanol. The 20% aqueous methanol solution is then extracted with carbon tetrachloride and the carbon tetrachloride extract (E) is discarded.

The 20% aqueous methanol extract is then further diluted with water to yield a 40% aqueous methanol solution which is then extracted with chloroform.

The chloroform extract is separated, and the solvent removed to yield residue (F). The residue (F) is then purified by column chromatography. The column, suitably a silica gel column, most suitably a SilicAR CC-7 column is prepared in chloroform. The fractions coming off in chloroform, in five column volumes of .5% methanol in chloroform, and in approximately five column volumes of 1% methanol in chloroform are discarded, the next approximately 1-2 column volumes of 1% methanol in chloroform are retained as fraction H and the following 1–2 column volumes of 1% methanol in chloroform are retained as Fraction I. Further elution with the same solvent (1–2 C.V.) yields fraction J.

Upon evaporation of the solvent the residual fraction H is rich in bruceantin and contains some dehydro bruceantin, whereas the following fraction I contains some bruceantin and is rich in bruceantarin.

Fraction H is then rechromatographed, suitably, the chromatography is carried out on a silica gel column preferably utilizing SilicAR CC-7. The column is eluted with increasing proportions of ether in benzene. Elution with up to 20% ether in benzene yields no desirable fractions. Elution with 30% ether in benzene (circa 4 to 5 column volumes) yields an eluate which upon evaporation gives a residue (e) which contains some bruceantin. Further elution with the same solvent (8 to 10 column volumes) yielded fraction (f) which on evaporation yields a residue of substantially pure bruceantin. Further elution with the same solvent (circa 4 to 5 column volumes) yields fraction (g) which upon evaporation yields a residue comprising substantially pure dehydrobruceantin.

Chromatography of fraction I on SilicAR CC-7 utilizing benzene and in increasing amounts of ether yields on elution with column volumes of 30% ether/benzene substantially pure bruceantarin. Further elution with the same solvent yields first a new simaroubolide havin antitumor activity followed by isobruceine B.

Chromatography of fraction J on SilicAR CC-7 utilizing benzene and increasing amounts of ether yields on elution with 60% ether/benzene substantially pure Bruceine B.

Bruceantin itself does not crystallize readily. A crystalline derivative, the triacetate, has been prepared in the usual manner.

The alcoholic extract A showed activity against P388 leukemia in mice and Walker 256 carcinoma in rats.

Bruceantin showed significant activity against the P-388 leukemia in a range of 15 to 2,000 $\mu$g/Kg. In vitro testing against cells derived from human carcinoma of the nasopharynx (KB cells) cytotoxicity ($ED_{50}$) was noted at a level of about $10^{-3}$ $\mu$g/ml.

The modes contemplated by the inventor of carrying out the invention include pharmaceutical compositions and processes of administration thereof.

Solutions of the principal active ingredient can be prepared in water or in water suitably diluted with, for example, ethanol, glycerin, edible polyols (for example, glycerine, polyethylene glycols, propylene glycol), and the like. Dispersions can be prepared in glycerol, liquid polyethylene glycols, and mixture thereof, and in oils.

Under ordinary conditions of storage and use, these preparations contain a preservative to prevent the growth of microorganisms.

As stated above, the pharmaceutical compositions can be in forms suited for injectable use which forms include sterile aqueous solutions or dispersions and sterile powders for the extemporaneous preparation of sterile injectable solutions or dispersions. In all cases, the form must be sterile and must be fluid to the extent that easy syringeability exists. It must be stable under the conditions or manufacture and storage must be preserved against the contaminating action of microorganism such as bacteria and fungi. The basic solvent or dispersion medium can contain water, ethanol, polyols (for example, glycerol, propylene glycol, and liquid polyethylene glycol, and the like), suitable mixtures thereof, and vegatable oils. The proper fluidity can be maintained, for example, by the use of a coating, such as lecithin, by the maintenance of the required particle size in the case of dispersions and by the use of surfactants (for example, a condensation product of ethylene oxide with fatty acids or fatty alcohols, partial esters of fatty acids and a hexitol anhydride, and polyoxethylene condensation products of the esters). The prevention of the action of microorganisms can be brought about by various antibacterial and antifungal agents, for example, parabens, chlorobutanol, benzyl alcohol, phenol, sorbic acid, thermerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the principal active ingredient in the required amount in the appropriate solvent with various of the other ingredients enumerated above, as required, followed by filter sterilization. Generally, dispersions are prepared by incorporating the previously sterilized active ingredient into a sterile vehicle which contains the basic dispersion medium and the required other ingredients from those enumerated above.

In the case for sterile powders for the preparation of sterile injectable solutions the preferred method of preparation is the freeze-drying technique which yield a powder of the active ingredient plus any additional desired ingredients from a previously sterile-filtered solution thereof. The powders can also be sterilized by the use of a gas, for example, ethylene oxide and subsequently incorporated, with the required additional ingredients and in the proper particle size, into the basic powder for later reconstitution with the desired suspending liquid which, of course, itself must be sterile.

Supplementary active ingredients can be incorporated into the inventive compositions. These ingredients include for example, mechorethamine hydrochloride and 5-bis (2-chloroethyl) amino-uracil; triethylene melamine; actinomycin C; cycloheximide.

It is especially advantageous to formulate the inventive compositions in dosage unit form for ease of administration and uniformity of dosage. Dosage unit form as used in the specification and claims herein refers to physically discrete units suited as unitary dosages for the animal and human subjects to be treated, each unit containing a predetermined quantity of active material calculated to produce the desired therapeutic effect in association with the required pharmaceutical carrier. The specifications for the novel dosage unit forms of this invention are dictated by and directly dependent of (a) the unique characteristics of the active material and the particular therapeutic effect to be achieved and (b) the limitations inherent in the art of compounding such an active material for the treatment of disease in living subjects having a diseased condition in which bodily health is impaired as disclosed in detail in this specification, these being features of the present invention.

The dosage of the principal active ingredient for the treatment of the indicated condition depends on the age, weight, and condition of the subject being treated, the particular condition and its severity, the particular form of the active ingredient and the route of administration. A dose of from about 100 µg/kg or a daily total dose of from about 5 to about 20 mg. given singly or in individually smaller doses is deemed suitable.

The principal active ingredient is compounded for convenient and effective administration in effective amounts with a suitable pharmaceutically acceptable carrier in dosage unit form as hereinbefore described. A unit dosage form can contain the principal active ingredient in amounts ranging from about 1 to about 5 mg. per unit. Expressed in proportions the active ingredient is present in from about 0.01 to about 0.1% w./v. of the liquid compositions.

Melting points were determined on a Fisher-Johns melting point apparatus and are corrected. Ultraviolet absorption spectra were determined on Beckmann Model DK-2A and Coleman Hitachi Model EPS-3T recording spectrophotometers. Infrared spectra were determined on a Perkin-Elmer Model 257 recording spectrophotometer. Nuclear magnetic resonance spectra were determined on a Varian HA-100 spectrometer with tetramethylsilane as an internal standard. Mass spectra were obtained from Hitachi Perkin-Elmer Model RMU-6E and AEI Model MS-902 spectrometers. Values of $[\alpha]_D$ were determined on a Perkin-Elmer Model 141 automatic polarimeter. Microanalyses were carried out by Spang Microanalytical Laboratory, Ann Arbor, Michigan. Petroleum ether refers to the fraction with bp 60–68°. All thin layer chromatography was carried out on prepared plates (Brinkmann, Mallinckrodt and Camag) and were visualized first with 5% ferric chloride in 95% ethanol followed by vanillin (25% vanillin in ethanol: conc. sulfuric acid — 1:5).

EXAMPLE I

Isolation of Bruceantin Concentrate

The concentrated alcoholic extract from 10 kg of dried ground stem bark (A, 1180 g) was partitioned between water (6 l) and chloroform (6 l). The water layer was washed with chloroform (6 l) and the combined chloroform layers were evaporated to give a brown tar (B, 385 g). Evaporation of the water layer gave a brown tar (C, 630 g). Fraction B was partitioned between 15% aqueous methanol (6 L). and petroleum ether (4 × 4 l). Concentration of the petroleum ether layer gave a dark green tar (D, 189 g). The 10% aqueous methanol layer was diluted with water to 20% aqueous methanol and extracted with carbon tetrachloride (4 × 3.8 l). The combined carbon tetrachloride layer was evaporated to afford a green tar (E, 70 g) and the 20% aqueous methanol layer was diluted with water to 40% aqueous methanol and extracted with chloroform (5 × 2.4 l). The combined chloroform layer was evaporated to give a brown tar (F, 90 g) and the 40% aqueous methanol layer was evaporated to give a brown powder (G, 10 g). In this way all of the activity (KB and P-388) was effectively concentrated in the final chloroform layer (fraction F).

EXAMPLE II

Preliminary Chromatographic Purification

Fraction F was chromatographed on a column of SilicAR CC-7 (5.4 Kg, column solvent Volume :~9 l.) and eluted with first chloroform and then increasing amounts of methanol in chloroform. (45 l. methanol/chloroform, 5:995; 60 l. methanol/chloroform, 1:99) Fractions were combined on the basis of the similarity on Chromar 7GF plates (20 × 20 cm, 0.25 mm) developed with 2:3 ether in benzene and visualized with ferric chloride and vanillin sprays. (Bruceantin, bruceantarin, bruceine C and bruceine B were eluted in that order respectively, from the column and were visualized as dark grey to black spots on spraying the plates with ferric chloride). Continued elution with methanol/chloroform (15 l, 1:99) gave a fraction (H, 8.1 g) enriched in bruceantin. Continued elution with methanol/chloroform (15 l, 1:99) gave a bruceantarin enriched fraction (I, 4.8 g) and finally elution with methanol/chloroform (30 l, 1:49) gave a fraction (J, 3.6 g) containing bruceine B.

EXAMPLE III

Isolation of Bruceantin (1)

Careful column chromatography of fraction H on SilicAR CC-7 (600 g, column solvent volume ~1 l.) with benzene as eluant followed by benzene containing increasing amounts of ether (2 l, ether/benzene 3:97; 4 l. ether/benzene, 3:47; 4 l. ether/benzene 1:9; 20 l. ether/benzene 1:4) gave fractions of no interest which were discarded. Further elution with ether/benzene (4.4 l, 3:7) yielded fraction E containing some bruceantin, further elution with the same solvent (8 l, 3:7) yielded pure bruceantin (1, 2.0 g, 0.02%) as a colorless foam. Attempts at crystallization of bruceantin from many solvents failed and all spectra were determined on samples freshly prepared by preparative thin layer chromatography (same conditions as analytical thin layer chromatography) and showed: $[\alpha]_D^{25}$ −27.7° (c 3.0, pyridine); uv $\lambda_{max}^{EtOH}$ 280 ($\epsilon$ 6,450) and 221 nm ($\epsilon$ 14,100); uv $\lambda_{max}^{EtOH + NaOH}$ 328 ($\epsilon$ 4,260) and 221 nm ($\epsilon$ 15,500); ir $\lambda_{max}^{KBr}$ 2.90, 5.76, 6.05, 6.13, 8.70 and 9.45 $\mu$; mass spectrum m/e 548 (M$^+$), 438, 420, 402, 297, 151, 111.0819 (calcd. for C$_7$H$_{11}$O, 111.0809); nmr (CDCl$_4$) $\tau$8.88 (6H, d, $\underline{J}$ = 6.5 Hz,CH(CH$_3$)$_2$), 8.56 (3H, s, 10-CH$_3$), 8.11 (3H,br. s, 4-CH$_3$), 7.82 (3H, s, -CH=C(CH$_3$)-), 7.29 (1H, br.m, OH), 6.47 (1H,br.m, OH), 6.24 (3H, s, OCH$_3$), 4.39 (1H, br.s, OCOCH=C(CH$_3$)-), 3.87 (1H,br.s, OH), and 3.79 (1H, d, $\underline{J}_{15,14}$ = 13 Hz, 15-H). Anal. High resolution mass spectrum calcd. for C$_{28}$H$_{36}$O$_{11}$: M$^+$ = 548.225; found 548.222.

Continued elution with ether/benzene (5 l, 3:7) gave a second component as a colorless foam which was identified as dehydrobruceantin (5, 375 mg, 0.003%): $[\alpha]_D^{25}$ 79.0° (c 0.62, pyridine); uv $\lambda_{max}^{EtOH}$ 295 (sh) ($\epsilon$ 2,000), and 255 nm ($\epsilon$ 12,000); uv $\lambda_{max}^{EtOH + NaOH}$ 340 ($\epsilon$ 1,800), 263 ($\epsilon$ 6,900) and 225 nm ($\epsilon$ 25,000); ir $\lambda_{max}^{KBr}$ 290, 5.78, 6.18, 8.07, 8.62 and 9.45 $\mu$; mass spectrum m/e 546 (M$^+$), 528, 436, 418, 400, 297, 151, 149, 111 and 95; nmr (CDCl$_3$) 8.95 (6H, d, $\underline{J}$ = 7Hz, CH(CH$_3$)$_2$), 8.38 (3H, s, 10-CH$_3$), 8.01 (3H, s, 4-CH$_3$), 7.92 (3H, s, -CH=C(CH$_3$)-), 6.32 (3H, s, OCH$_3$), 4.26 (1H,br.s, OCOCH=C(CH$_3$)-), and 4.13 (1H, d, J$_{15,14}$ = 13Hz, 15-H).

EXAMPLE IV

Isolation of Bruceantarin (2)

Careful column chromatography of fraction I (4.8 g) on SilicAR CC-7 (330 g) using benzene followed by benzene containing increasing amounts of ether gave in the fraction eluted with ether/benzene (10 l; 3:7) crystalline bruceantarin (2). The combined crystalline fractions (560 mg) were dissolved in chloroform and tested with activated charcoal then filtered and evaporated to give a colorless glass (320 mg). This material was recrystallized from ethylene chloride - benzene to give pure bruceantarin (2, 280 mg, 0.003%): mp 182°–185°; $[\alpha]_D^{25}$ −20.7° (c 0.6, pyridine); uv $\lambda_{max}^{EtOH}$ 278 ($\epsilon$ 7,000) and 231 nm ($\epsilon$ 10,500); uv $\lambda_{max}^{EtOH + NaOH}$ 330 ($\epsilon$ 4,480) and 230 nm ($\epsilon$ 9,030); ir $\lambda_{max}^{KBr}$ 2.9, 5.78, 6.03, 6.08, 6.12, 7.88, 8.70, 9.0, 9.45, and 13.8 $\mu$; mass spectrum m/e 542 (M$^+$), 437, 420, 402, 297, 151, 105 and 77; nrm (CDCl$_3$) $\tau$ 8.63 (3H, s, 10-CH$_3$), 8.20 (3H, br.s, 4-CH$_3$), 6.56 (3H, s, OCH$_3$), 3.58 (1H, d, $\underline{J}_{15,14}$ = 13Hz, 15-H), 2.60 (3H, m, B$_2$X portion of A$_2$B$_2$X, m and p-benzoate protons), and 2.07 (2H, d of d, A$_2$ part of A$_2$B$_2$X system,$\underline{J}_{AB}$ = 7.5Hz, J$_{AX}$ = 1.5Hz, o-benzoate protons). Anal. Calcd for C$_{28}$H$_{30}$O$_{11}$: C, 61.99; H, 5.57. Found: C, 62.06; H, 5.60.

Further elution with ether/benzene (8 l, 3:7) gave a fraction (490 mg) enriched in a new simaroubolide. This material was applied to twenty Chromar 7GF plates (20 × 20 cm, 0.25 mm) and developed with 2% isopropanol in methylene chloride 2 times to give in the major band 220 mg of a colorless foam. This material showed $[\alpha]_D^{24}$ −14.5° (c 0.44, pyridine); uv $\lambda_{max}^{EtOH}$ 278 ($\epsilon$ 6,650) and 220nm ($\epsilon$ 14,100); uv $\lambda_{max}^{EtOH + NaOH}$ 328 ($\epsilon$ 3,230) and 225 nm ($\epsilon$ 10,000); ir $\lambda_{MBL}^{KBr}$ 2.90, 5.80, 6.11, 7.95, 8.65, 9.47 $\mu$; mass spectrum m/e 547, 546, 438, 420, 402, 151, 127, 110, and 109; nmr (CDCl$_3$) $\tau$ 6.28, 7.90, 8.02, 8.19, 8.50, 8.63 (methyl singlets).

Continued elution with ether/benzene (10l, 1:1) resulted in the isolation of a second crystalline fraction identified as iso-bruceine B (6). The combined crystalline fractions (1.0 g) were dissolved in chloroform and treated with activated charcoal filtered and evaporated to give a colorless glass (600 mg). This material was recrystallized from ether-methylene chloride to afford colorless needles of iso-bruceine B (6, 360 mg, 0.004%): mp: 243°–246°; $[\alpha]_D$ −36.2° (c 0.24, pyridine); uv $\lambda_{max}^{EtOH}$ 242 nm ($\epsilon$ 8,850); ir $\lambda_{max}^{KBr}$ 2.85, 5.75, 6.01, 6.08, 8.00, 8.20, 8.65, 9.42, and 10.3 $\mu$; mass spectrum m/e 480 (M$^+$), 478, 462, 438, 420, 402, 346, 314, 297, 151, 135 and 95; nmr (pyr-d$_5$) $\tau$ 8.74 (34, s, 10-CH$_3$), 8.30 (3H, br.s, 4-CH$_3$), 8.02 (3H, s, OCOCH$_3$), 6.38 (3H, s, OCH$_3$), 5.93 (1H, s), 4.08 (1H, br.s,3-H), and 3.52 (1H, d, $\underline{J}_{15,14}$ = 13Hz, 15-H). Anal. calcd for C$_{23}$H$_{28}$O$_{11}$.H$_2$O: C, 55.41; H, 6.06. Found: C, 54.96; H, 6.07.

EXAMPLE V

Bruceantin triacetate (6)

Bruceantin (1, 50 mg) was dissolved in a mixture of acetic anhydride (0.9 ml) and dry pyridine (0.9 ml) and the resulting solution was stirred for 40 hours at room temperature. After this time the reaction mixture was poured into a mixture of ice and dilute hydrochloric acid and stirred for 5 min., then extracted with chloroform. The chloroform layer was washed with saturated sodium bicarbonate, water and saturated sodium chloride, then dried over magnesium sulfate and evaporated to give 70 mg of a pale yellow glass. This material was applied to three Chromar 7GF plates (20 × 20 cm × 0.25 mm) and eluted with 1:1 ether/benzene to give in the major band bruceantin triacetate (6, 44 mg, 72%) as an amorphous powder which was crystallized from methanol-water to give fine colorless crystals of 6: uv $\lambda_{max}^{EtOH}$ 250 nm ($\epsilon$ 11,200); ir $\lambda_{max}^{KBr}$ 5.74, 5.95, 6.13, 8.20, 8.66, and 9.50 $\mu$; mass spectrum m/e 674 (M$^+$), 632, 590, 572, 530, 480, 438, 434, 420, 402, 297, 151, 111, and 95; nmr (CDCl$_3$) $\tau$ 8.95 (6H, d, $\underline{J}$ = 7HZ, CH(C$\underline{H}_3$)$_2$), 8.55 (3H, s, 10-C$\underline{H}_3$), 8.24 (3H, s, 4-C$\underline{H}_3$), 8.03 (3H, br. s, -CH=C(C$\underline{H}_3$)-), 7.79, 7.89 (9H, 2s, OCOC$\underline{H}_3$), 6.34 (3H, s, OC$\underline{H}_3$), and 4.46 (1H, br.s, OCOC$\underline{H}$=C(CH$_3$)-).

I claim:

1. In a process of producing bruceantin, the sequential steps comprising:
   a. extracting Brucea antidysenterica with an alkanol,
   b. partitioning said alkanoic extract between chloroform and water,
   c. removing the solvent from the chloroform fraction and partitioning said fraction between 10% aqueous methanol and petroleum ether,
   d. separating said 10% aqueous methanol fraction and adding thereto sufficient water to produce a 20% aqueous methanol solution and extracting same with carbon tetrachloride,
   e. further diluting said 20% aqueous methanol solution with sufficient water to provide a 40% aqueous methanol solution and extracting same with chloroform,
   f. removing the chloroform, chromatographing on silica gel and eluting with chloroform containing up to 0.5% methanol,
   g. eluting with 1% methanol in chloroform and collecting the first fractions which contain a compound which upon thin layer chromatography gives an immediate dark stain with ferric chloride.

2. A method according to claim 1 additionally comprising the step of removing the solvent from the fractions showing the immediate ferric chloride reaction of step (g) to provide a concentrate comprising bruceantin.

3. A method of claim 2 further comprising chromatograhing the product of claim 2 on silica gel and eluting with 30% ether/benzene and collecting the first fraction which contains a compound which, upon thin layer chromatography, gives an immediate dark stain with ferric chloride.

4. A method of claim 3 additionally comprising the step of removing the solvent.

5. A compound designated bruceantin having the formula.

wherein R$_2$ is hydrogen

* * * * *